(12) United States Patent
Stricko, III et al.

(10) Patent No.: US 11,589,939 B2
(45) Date of Patent: Feb. 28, 2023

(54) SYSTEMS AND METHODS FOR GUIDED PORT PLACEMENT SELECTION

(71) Applicant: INTUITIVE SURGICAL OPERATIONS, INC., Sunnyvale, CA (US)

(72) Inventors: Robert G. Stricko, III, Sunnyvale, CA (US); Brandon D. Itkowitz, San Jose, CA (US); Amy E. Kerdok, San Jose, CA (US); Brett M. Page, Santa Clara, CA (US); Jason A. Pile, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 350 days.

(21) Appl. No.: 16/759,073

(22) PCT Filed: Oct. 17, 2018

(86) PCT No.: PCT/US2018/056267
§ 371 (c)(1),
(2) Date: Apr. 24, 2020

(87) PCT Pub. No.: WO2019/089226
PCT Pub. Date: May 9, 2019

(65) Prior Publication Data
US 2020/0345438 A1 Nov. 5, 2020

Related U.S. Application Data

(60) Provisional application No. 62/579,722, filed on Oct. 31, 2017, provisional application No. 62/579,407, (Continued)

(51) Int. Cl.
A61B 34/10 (2016.01)
B25J 9/16 (2006.01)
(Continued)

(52) U.S. Cl.
CPC ............. *A61B 34/70* (2016.02); *A61B 34/10* (2016.02); *A61B 34/35* (2016.02); *A61B 34/37* (2016.02);
(Continued)

(58) Field of Classification Search
CPC ......... A61B 34/70; A61B 34/10; A61B 34/35; A61B 34/37; A61B 2034/105;
(Continued)

(56) References Cited

U.S. PATENT DOCUMENTS 8,282,653 B2 10/2012 Nelson et al.
2011/0199302 A1* 8/2011 Tossell .................. A63F 13/213
345/158

(Continued)

FOREIGN PATENT DOCUMENTS

KR 101539270 B1 7/2015
WO WO-2015142943 A1 9/2015

OTHER PUBLICATIONS

Adhami et al., Optimal Planning for Minimally Invasive Surgical Robots, 2003 (Year: 2003).*
(Continued)

Primary Examiner — Phong X Nguyen
(74) Attorney, Agent, or Firm — Haynes and Boone, LLP

(57) ABSTRACT

A computing device comprises a memory and a control unit coupled to the memory. The control unit is configured to receive a patient model and identify a plurality of port locations on the patient model for accessing a workspace using a plurality of instruments controlled by a computer-assisted device. For each of the port locations, the control unit determines a collision volume for portions of the computer-assisted device proximal to the port location, a reachability metric, and an anthropomorphic metric. For each combination of the plurality of port locations, the (Continued)

control unit determines a collision metric based on overlaps of the collision volumes for the port locations in the combination, and an aggregate metric for the combination. The control unit is also configured to display one or more of the combinations of the plurality of port locations to a user along with a corresponding aggregate metric.

20 Claims, 6 Drawing Sheets

Related U.S. Application Data filed on Oct. 31, 2017, provisional application No. 62/578,652, filed on Oct. 30, 2017, provisional application No. 62/579,056, filed on Oct. 30, 2017.

(51) Int. Cl.
| | |
|---|---|
| *A61B 34/00* | (2016.01) |
| *A61B 34/35* | (2016.01) |
| *A61B 34/37* | (2016.01) |
| *B25J 17/02* | (2006.01) |
| *A61B 34/30* | (2016.01) |
| *G06T 15/08* | (2011.01) |
| *G06T 17/00* | (2006.01) |

(52) U.S. Cl.
CPC ........... *B25J 9/1666* (2013.01); *B25J 9/1689* (2013.01); *B25J 17/0283* (2013.01); *A61B 2034/105* (2016.02); *A61B 2034/107* (2016.02); *A61B 2034/301* (2016.02); *G06T 15/08* (2013.01); *G06T 17/00* (2013.01); *G06T 2210/21* (2013.01)

(58) Field of Classification Search
CPC ........ A61B 2034/107; A61B 2034/301; A61B 34/30; A61B 17/34; A61B 2034/101; B25J 9/1666; B25J 9/1689; B25J 17/0283; G06T 15/08; G06T 17/00; G06T 2210/21
See application file for complete search history.

(56) References Cited

U.S. PATENT DOCUMENTS

| | | | | |
|---|---|---|---|---|
| 2014/0135985 | A1* | 5/2014 | Coste-Maniere | A61B 34/30 700/255 |
| 2015/0025549 | A1* | 1/2015 | Kilroy | A61B 90/10 606/130 |
| 2015/0230689 | A1* | 8/2015 | Blohm | A61B 1/00147 600/118 |
| 2016/0070436 | A1* | 3/2016 | Thomas | A61B 8/0808 715/771 |
| 2016/0314710 | A1* | 10/2016 | Jarc | G09B 23/28 |
| 2017/0265943 | A1* | 9/2017 | Sela | A61B 34/20 |
| 2017/0265947 | A1* | 9/2017 | Dyer | A61B 6/501 |
| 2017/0282372 | A1 | 10/2017 | Itkowitz et al. | |
| 2019/0231460 | A1* | 8/2019 | DiMaio | B25J 9/1676 |
| 2019/0307510 | A1* | 10/2019 | Rotenberg | G06T 17/00 |
| 2020/0345438 | A1* | 11/2020 | Stricko, III | A61B 34/10 |
| 2022/0167868 | A1* | 6/2022 | Sela | A61B 17/3421 |

OTHER PUBLICATIONS

Joseph et al., "Chopstick" surgery: a novel technique improves surgeon performance and eliminates arm collision in robotic single-incision laparoscopic surgery, 2010 (Year: 2010).*
Pisla et al., Kinematics and workspace modeling of a new hybrid robot used in minimally invasive surgery, 2012 (Year: 2012).*
Sun et al., Port placement and pose selection of the da Vinci surgical system for collision-free intervention based on performance optimization, 2007 (Year: 2007).*
Weede et al., Knowledge-based System for Port Placement and Robot Setup Optimization in Minimally Invasive Surgery, 2012 (Year: 2012).*
Extended European Search Report for Application No. EP18872825.7 dated Jul. 9, 2021, 11 pages.
Internationai Preliminary Report on Patentability for Application No. PCT/US2018/056267, dated May 14, 2020, 8 pages.
International Search Report and Written Opinion for Application No. PCT/US2018/056267, dated May 7, 2019, 12 pages (ISRG11580/PCT).
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR GUIDED PORT PLACEMENT SELECTION

CROSS-REFERENCE TO RELATED APPLICATIONS

This application is the U.S. National Phase of International Patent Application No. PCT/US2018/056267, filed Oct. 17, 2018, which designated the U.S. and claims priority to and benefit of U.S. Provisional Patent Application No. 62/578,652, filed Oct. 30, 2017, entitled "Systems and Methods for Guided Port Placement Selection"; U.S. Provisional Patent Application No. 62/579,056, filed Oct. 30, 2017, entitled "Systems and Methods for Guided Port Placement Selection"; U.S. Provisional Patent Application No. 62/579,407, filed Oct. 31, 2017, entitled "Systems and Methods for Guided Port Placement Selection"; and U.S. Provisional Patent Application No. 62/579,722, filed Oct. 31, 2017, entitled "Systems and Methods for Guided Port Placement Selection"; all of which are incorporated by reference herein in their entirety.

TECHNICAL FIELD

The present disclosure relates generally to teleoperation of devices with moveable arms having end effectors and more particularly to systems and methods for guiding the selection of port placements in a workspace.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more repositionable arms and/or end effectors. It is also common to operate the electronic devices via teleoperation using one or more input control devices on an operator workstation to control the motion and/or operation of the repositionable arms and/or the end effectors. When these teleoperated devices are used to perform procedures in a workspace with limited access points through which the end effectors are inserted and then teleoperated, the location of the access points is important to successfully performing the procedure. For example, when the end effectors are medical instruments being used to perform a minimally-invasive surgical procedure, the end effectors are typically inserted into the patient through one or more small orifices or incision sites that may be referred to as ports. The location of the ports is important as their location limits which portions of the patient's interior anatomy may be reached using the end effectors, the likelihood that the end effectors and/or repositionable arms may collide, the ease with which an operator (e.g., a surgeon) may teleoperate the end effectors, and/or the like. Port placement is typically subject to tradeoffs as good port placement for reaching target anatomy within the patient may also result in a high likelihood of collisions, reduced operability, and/or the like. In addition, a good port placement for one patient and/or procedure may not be as good for a different patient and/or procedure due to differences in patient anatomy, target tissue structures, and/or the like.

Accordingly, it would be advantageous to have systems and methods to aid in the selection and placement of ports for a minimally invasive procedure that account for and/or allow for tradeoffs between the factors affecting the quality and appropriateness of various port placement locations.

SUMMARY

Consistent with some embodiments, a method performed by a control unit includes receiving a patient model, identifying a plurality of port locations on the patient model for accessing a workspace using a plurality of instruments controlled by a computer-assisted device, displaying one or more of the combinations of the plurality of port locations to a user along with a corresponding aggregate metric. For each of the port locations, the method includes determining a collision volume for portions of the computer-assisted device proximal to the port location, a reachability metric, and an anthropomorphic metric. For each combination of the plurality of port locations, the method includes determining a collision metric based on overlaps of the collision volumes for the port locations in the combination, and an aggregate metric for the combination.

Consistent with some embodiments, a computing device includes a memory and a control unit coupled to the memory. The control unit is configured to receive a patient model, identify a plurality of port locations on the patient model for accessing a workspace using a plurality of instruments controlled by a computer-assisted device, and display one or more of the combinations of the plurality of port locations to a user along with a corresponding aggregate metric. For each of the port locations, the control unit is configured to determine a collision volume for portions of the computer-assisted device proximal to the port location, a reachability metric, and an anthropomorphic metric. For each combination of the plurality of port locations, the control unit is configured to determine a collision metric based on overlaps of the collision volumes for the port locations in the combination, and an aggregate metric for the combination.

Consistent with some embodiments, a method includes receiving a model of a patient, identifying a kinematic measure for a teleoperated system, receiving a human factors constraint for use of the teleoperated system, and establishing a set of port placement locations for the teleoperated system on the model based on the kinematic measure and the human factors constraint.

Consistent with some embodiments, a non-transitory machine-readable medium comprising a plurality of machine-readable instructions which when executed by one or more processors associated with a computing device are adapted to cause the one or more processors to perform any of the methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Figure 1:
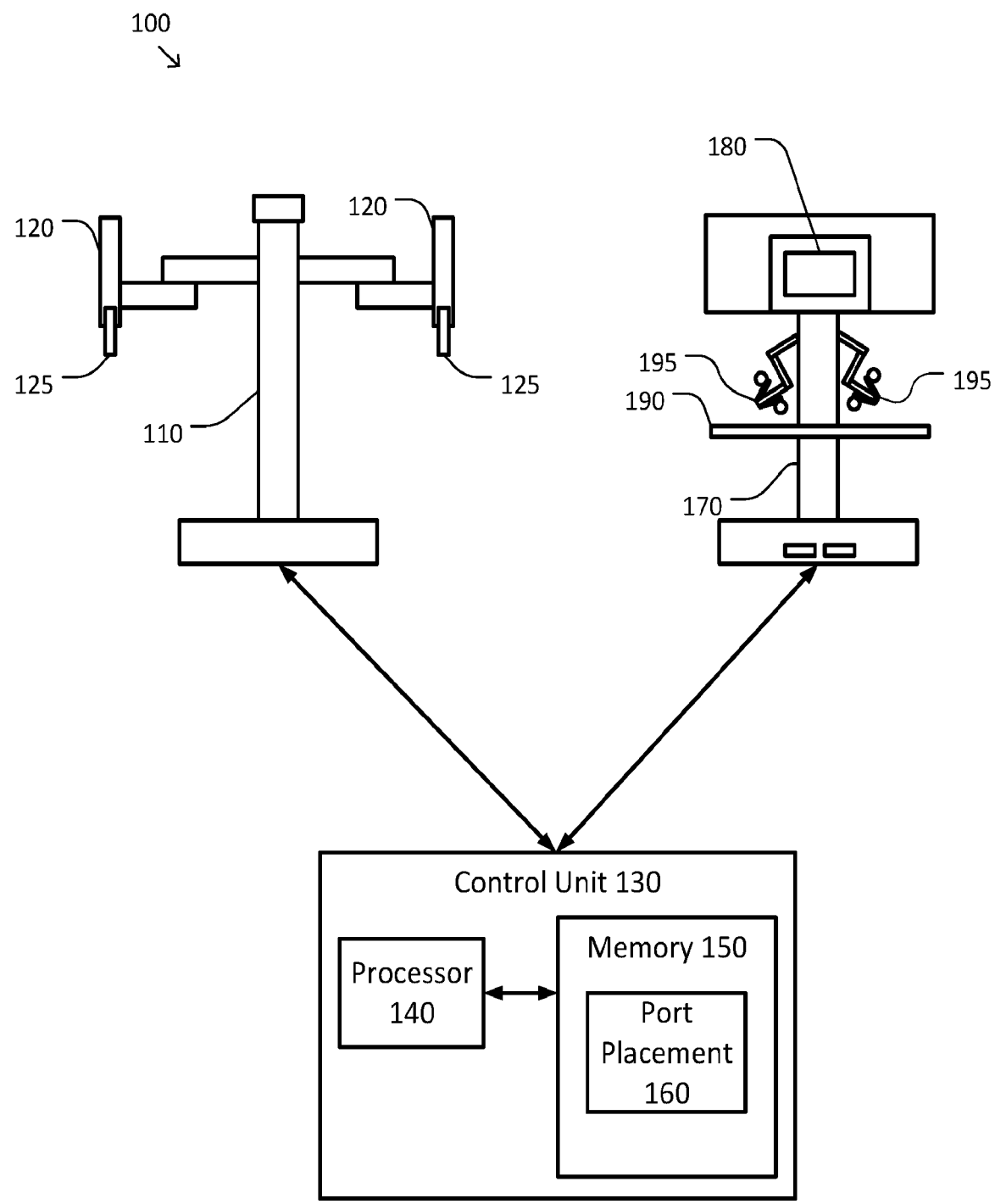
FIG. 1 is a simplified diagram of a computer-assisted system according to some embodiments.

In the figures, elements having the same designations have the same or similar functions.

DETAILED DESCRIPTION

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, and for a device with repositionable arms, the term "proximal" refers to a direction toward the base of the device and "distal" refers to a direction away from the base.

Aspects of the invention are described primarily in terms of an implementation using a da Vinci® Surgical System (specifically, a Model IS4000, marketed as the da Vinci® Xi™ Surgical System), commercialized by Intuitive Surgical. Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000; the Model IS4200, commercialized as the da Vinci® X™ Surgical System) are merely exemplary and are not to be considered as limiting the scope of the inventive aspects disclosed herein. For example, any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperated systems.

FIG. 1 is a simplified diagram of a computer-assisted system 100 according to some embodiments. As shown in FIG. 1, computer-assisted system 100 includes a device 110 with one or more movable or repositionable arms 120. Each of the one or more repositionable arms 120 may support one or more end effectors 125. In some examples, device 110 may be consistent with a computer-assisted surgical device. The one or more end effectors 125 may include instruments, imaging devices, and/or the like. In some medical examples, the instruments may include medical instruments, such as clamps, grippers, retractors, cautery tools, suction tools, suturing devices, and/or the like. In some medical examples, the imaging devices may include endoscopes, cameras, ultrasonic devices, fluoroscopic devices, and/or the like.

Device 110 is coupled to a control unit 130 via an interface. The interface may include one or more cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a port placement module 160 that may be used to support the identification and selection of ports for operating the one or more end effectors 125 within a workspace, such as the interior anatomy of a patient, as is described in further detail below with respect to FIG. 3.

Control unit 130 may further be coupled to an operator workstation 170 via the interface. Operator workstation 170 may be used by an operator, such as a surgeon, to control the movement and/or operation of the repositionable arms 120 and the end effectors 125. To support operation of the repositionable arms 120, operator workstation 170 includes a display system 180 for displaying images of at least portions of one or more of the repositionable arms 120 and/or end effectors 125. For example, display system 180 may be used when it is impractical and/or impossible for the operator to see the repositionable arms 120 and/or the end effectors 125 as they are being used. Operator workstation 170 may further include a console workspace with one or more input control devices 195 (sometimes called master control devices 195) that may be used for operating the device 110, the repositionable arms 120, and/or the end effectors 125. Each of the input control devices 195 may be coupled to the distal end of their own repositionable arms so that movements of the input control devices 195 may be detected by operator workstation 170 and communicated to control unit 130. To provide improved ergonomics, the console workspace may also include one or more rests, such as an arm rest 190 on which operators may rest their arms while manipulating the input control devices 195. In some examples, the display system 180 and the input control devices 195 may be used by the operator to teleoperate the repositionable arms 120 and/or the end effectors 125. In some embodiments, device 110, operator workstation 170, and control unit 130 may correspond to a da Vinci® Surgical System commercialized by Intuitive Surgical, Inc. of Sunnyvale, Calif.

In some embodiments, other configurations and/or architectures may be used with computer-assisted system 100. In some examples, control unit 130 may be included as part of operator workstation 170 and/or device 110. In some embodiments, computer-assisted system 100 may be found in an operating room and/or an interventional suite. And although computer-assisted system 100 includes only one device 110 with two repositionable arms 120, one of ordinary skill would understand that computer-assisted system 100 may include any number of devices with repositionable arms and/or end effectors of similar and/or different design from device 110. In some examples, each of the devices may include fewer or more repositionable arms 120 and/or end effectors 125. Additionally, although operator workstation 170 includes only two input control devices, one of ordinary skill would understand that operator workstation 170 may include any number of input control devices as well as other input devices, sensors, and/or the like.

Although not shown in FIG. 1, computer-assisted system 100 may further include one or more display devices and input devices for allowing the operator to view possible port placements, evaluate different port placements, and/or the like. In some examples, the possible display devices and input devices may include tablets, display screens, telestration systems, 3D displays, augmented reality systems, and/or the like.

Figure 2:
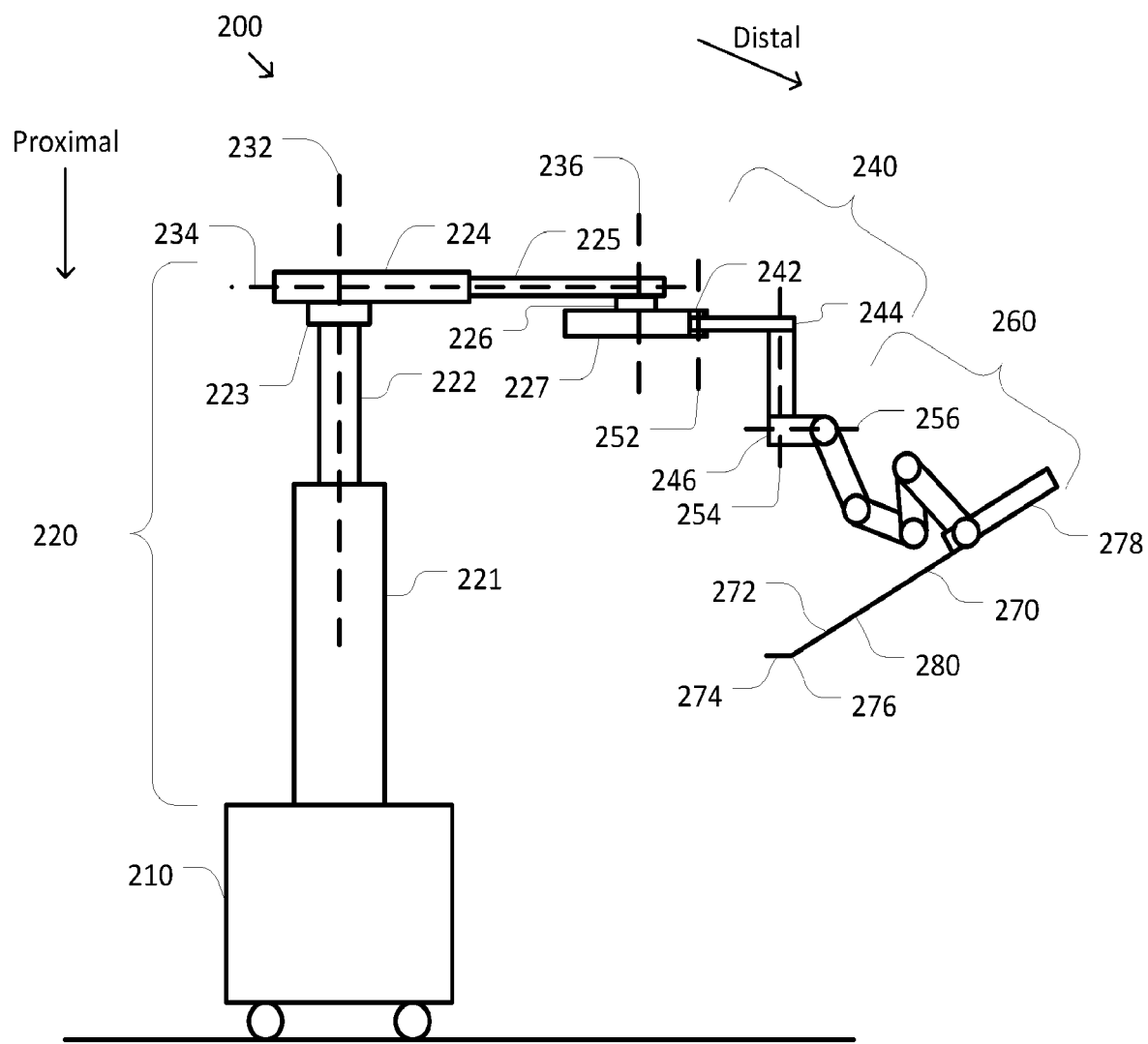
FIG. 2 is another simplified diagram of the computer-assisted system of FIG. 1 according to some embodiments.

FIG. 2 is a simplified diagram showing a computer-assisted device 200 according to some embodiments. For example, the computer-assisted device 200 may be consistent with computer-assisted device 110. As shown in FIG. 2, the computer-assisted device 200 includes various links and joints. The computer-assisted device generally has three different sets of links and joints. Starting at the proximal end with a mobile cart 210 is a set-up structure 220. Coupled to a distal end of the set-up structure is a series of set-up joints 240. And coupled to a distal end of the set-up joints 240 is a manipulator 260, such as a universal surgical manipulator. In some examples, the series of set-up joints 240 and manipulator 260 may correspond to one of the repositionable arms 120. And although computer-assisted device 200 is shown with only one series of set-up joints 240 and a corresponding manipulator 260, one of ordinary skill would understand that the computer-assisted device 200 may include more than one series of set-up joints 240 and corresponding manipulators 260 so that the computer-assisted device 200 is equipped with multiple repositionable arms. One of ordinary skill would also understand that the configurations for computer-assisted device 200 as shown in FIG. 2 are representative only and that port placement systems and methods described elsewhere herein are also applicable to computer-assisted devices having other configurations.

As shown, the computer-assisted device 200 is mounted on the mobile cart 210. The mobile cart 210 enables the computer-assisted device 200 to be transported from location to location, such as between operating rooms or within an operating room to better position the computer-assisted device 200 near a patient table. The set-up structure 220 is mounted on the mobile cart 210. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an orientation platform 227.

The links and joints of the set-up structure 220 include various degrees of freedom for changing the position and orientation (i.e., the pose) of the orientation platform 227. For example, the two-part column may be used to adjust a height of the orientation platform 227 by moving the shoulder joint 223 up and down along an axis 232. The orientation platform 227 may additionally be rotated about the mobile cart 210, the two-part column, and the axis 232 using the shoulder joint 223. The horizontal position of the orientation platform 227 may also be adjusted along an axis 234 using the two-part boom. And the orientation of the orientation platform 227 may also adjusted by rotation about an axis 236 using the wrist joint 226. Thus, subject to the motion limits of the links and joints in the set-up structure 220, the position of the orientation platform 227 may be adjusted vertically above the mobile cart 210 using the two-part column. The positions of the orientation platform 227 may also be adjusted radially and angularly about the mobile cart 210 using the two-part boom and the shoulder joint 223, respectively. And the angular orientation of the orientation platform 227 may also be changed using the wrist joint 226.

The orientation platform 227 may be used as a mounting point for one or more repositionable arms. The ability to adjust the height, horizontal position, and orientation of the orientation platform 227 about the mobile cart 210 provides a flexible set-up structure for positioning and orienting the one or more repositionable arms about a workspace, such as a patient, located near the mobile cart 210. FIG. 2 shows a single repositionable arm coupled to the orientation platform using a first set-up joint 242. And although only one repositionable arm is shown, one of ordinary skill would understand that multiple repositionable arms may be coupled to the orientation platform 227 using additional first set-up joints.

The first set-up joint 242 forms the most proximal portion of the set-up joints 240 section of the repositionable arm. The set-up joints 240 may further include a series of joints and links. As shown in FIG. 2, the set-up joints 240 include at least links 244 and 246 coupled via one or more joints (not expressly shown). The joints and links of the set-up joints 240 include the ability to rotate the set-up joints 240 relative to the orientation platform 227 about an axis 252 using the first set-up joint 242, adjust a height of the link 246 relative to the orientation platform along an axis 254, and rotate the manipulator at least about an axis 256 at the distal end of the link 246. The set-up joints 240 may further include additional joints, links, and axes permitting additional degrees of freedom for altering a position and/or orientation of the manipulator 260 relative to the orientation platform 227.

The manipulator 260 is coupled to the distal end of the set-up joints 240 and includes additional links and joints that permit control over a position and orientation of instrument 270 mounted at a distal end of the manipulator 260. Instrument 270 includes an elongate shaft 272 that is coupled between manipulator 260 and an end effector 274 via an optional articulated wrist 276. The degrees of freedom in the manipulator 260 may permit at least control of the roll, pitch, and yaw of the elongate shaft 272 relative to the distal end of the set-up joints 240. In some examples, the degrees of freedom in the manipulator 260 may further include the ability to advance and/or retreat elongate shaft 272 along an insertion carriage or spar 278 so as to move end effector nearer to or farther away from manipulator 260 along a longitudinal axis of instrument 270. Additional control over the orientation of end effector 274 relative to manipulator 260 may be controlled using optional wrist 276. In some examples, the degrees of freedom of the set-up joints 240 and the manipulator 260 may further be controlled so as to maintain a remote center 280 about a point on the instrument 270. In some examples, the remote center 280 may correspond to a port in a patient so that as the instrument 270 is used, the remote center 280 remains stationary to limit stresses on the anatomy of the patient at the remote center 280. In some examples, the manipulator 260 may be consistent with a universal surgical manipulator for use with the da Vinci® Surgical System commercialized by Intuitive Surgical. Inc. of Sunnyvale, Calif. In some examples, the instrument 270 may be an imaging device such as an endoscope, a gripper, a surgical tool such as a cautery or a scalpel, and/or the like.

Controlling the location where instrument 270 is inserted into a workspace, such as by inserting elongate shaft 272 through a cannula located at a port for accessing the interior anatomy of a patient, is important for the flexible and safe operation of computer-assisted device 200 and instrument 270. In some examples, if the location of the port is too close to target tissue, instrument 270 and end effector 274 may not have sufficient range of motion to access, interact with, and manipulate the target tissue. If the location of the port is too far from the target tissue, end effector 274 may not be able to reach the target tissue. If the location of the port is poorly chosen, there may be intervening tissues between the port and the target tissue which elongate shaft 272 and end effector 274 may not be able to maneuver around and/or elongate shaft 272 and end effector 274 may not have a comfortable or practical approach orientation to the target tissue. When computer-assisted device 200 includes multiple manipulators 260 and multiple instruments 270, the placement of their corresponding ports too close together may result in a higher likelihood of interference and/or collisions between the corresponding spars 278, manipulators 260, and/or other more proximal portions of computer-assisted device 200. Thus, controlling the port locations is important for providing access to a workspace for instruments 270, the avoidance of interference and collisions, ease of operability, and/or the like.

Traditional approaches to selecting port locations have typically relied on general port placement rules determined empirically from previous use of computer-assisted device 200 and, common sense based on a basic understanding of a workspace configuration, such as the typical anatomy of a patient for a surgical procedure. As an example, in the case of an upper abdominal surgery, recommendations for the port locations may include placing the port for an imaging device (e.g., an endoscope) at the umbilicus and locating additional ports along a diagonal line perpendicular to target anatomy and through the umbilicus along with a recommended spacing. Additional recommendations may include locating one or more of the ports above (superior to) or below (inferior to) the diagonal line to accommodate instruments 270 with different kinds of end effectors 274. And while these types of guidelines typically provide a good location for the ports, the guidelines do not always have sufficient flexibility to address variations in a workspace (e.g., patients with larger or smaller anatomy and/or patients with unusual anatomy due to previous procedures, the presence of lesions, and/or the like), variations in instruments and/or procedures, variations in operator preferences, and/or the like. Accordingly, improved systems and methods for aiding in the selection and location of ports that account for workspace variations, procedural variations, operator preferences, ease of operation, and/or the like are desirable.

Figure 3:
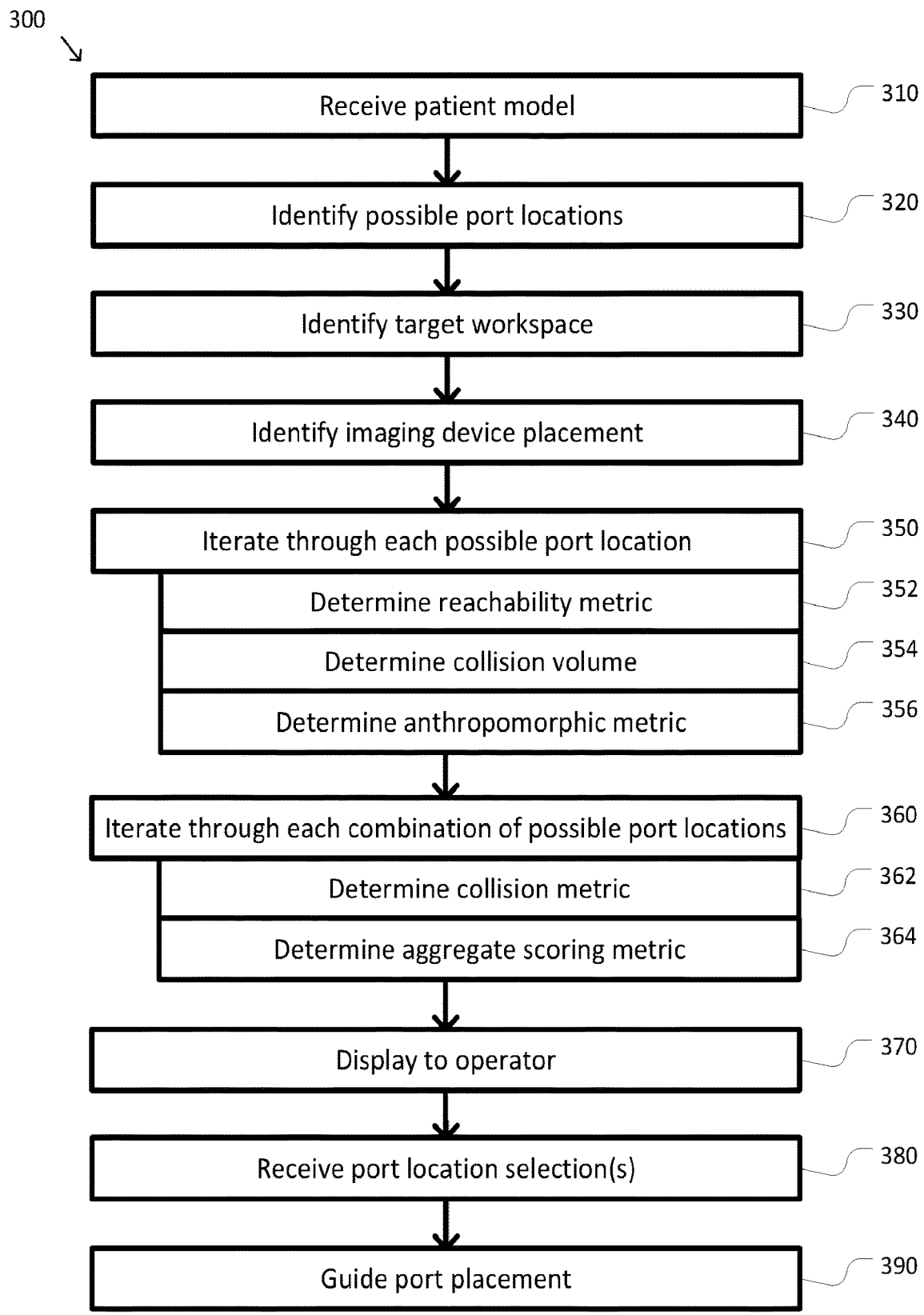
FIG. 3 is a simplified diagram of a method of selecting port locations according to some embodiments.

FIG. 3 is a simplified diagram of a method of selecting port locations according to some embodiments. One or more of the processes 310-390 of method 300 may be implemented, at least in part, in the form of executable code stored on non-transitory, tangible, machine-readable media that when run by one or more processors (e.g., the processor 140 in control unit 130) may cause the one or more processors to perform one or more of the processes 310-390. In some embodiments, method 300 may be performed by a module, such as port placement module 160. In some embodiments, method 300 may be used to identify port locations, evaluate each of the port locations, evaluate combinations of port locations, aid an operator in selecting and utilizing suitable port locations, and/or the like. In some examples, method 300 may be used to evaluate the port locations for one or more instruments, such as instrument 270, being teleoperated using a computer-assisted device, such as computer-assisted device 200. In some embodiments, process 340 is optional and may be omitted.

At a process 310, a patient model is received. The patient model represents the anatomy of the patient relevant to a current or planned procedure and can include internal target tissue and/or the exterior anatomy (e.g., dermis) of the patient through which one or more instruments, imaging devices, and/or the like are to be inserted through one or more ports. In some examples, the patient model may be obtained using a pre-operative scan of the patient using one or more of computer-aided tomography (CT), magnetic resonance imaging (MRI), ultrasound, 3D scanning (e.g., LIDAR) and/or the like. In some examples, the patient model may be obtained intraoperatively using a patient-side imaging or scanning system so as to adjust for changes in the anatomy of the patient due to the orientation of the patient (e.g., to account for the effects of gravity-based retraction), insufflation of the patient, and/or the like.

At a process 320, an initial set of possible port locations are identified. In some examples, knowledge about the target tissue for the procedure (e.g., a location of a lesion to be biopsied or resected) is mapped to the patient model data obtained during process 310 and a plurality of possible port locations are identified on the exterior anatomy of the patient. In some examples, the possible port locations are limited to those portions of the exterior anatomy that is within a threshold distance of the target anatomy so as to limit the possible port locations to those that are reachable using available surgical instruments. In some examples, the possible port locations may be limited based on general knowledge of anatomy, such as restricting port locations for an upper abdominal procedure to those located on an anterior portion of the patient anatomy below the rib cage and above the waist line. Each of the possible port locations may correspond to locations of existing orifices in the exterior anatomy of the patient and/or potential incision sites.

At a process 330, a target workspace is identified. In some examples, the location of the target tissue and the procedures to be performed on the target tissue are used to identify a procedure site envelope or workspace around the target tissue where one or more instruments are to be manipulated so as to access, grasp, manipulate, and/or otherwise interact with the target tissue. As an example, an end effector for grasping, stapling, and cutting may use a target workspace that includes room to approach the target tissue, articulate jaws into a desired orientation, move the jaws around the target tissue, perform the grasping, stapling, and cutting of the target tissue, and then retreat from the target tissue. In some examples, this target workspace may be determined using kinematic models of the corresponding instrument and end effector and identifying a swept volume through which the instrument and/or end effector moves to perform the procedure.

At an optional process 340, an imaging device placement is identified. In some examples, an intraoperative imaging device is often used to obtain live intraoperative images of the target tissue and/or target workspace for display to the operator so that the operator may observe one or more end effectors and the interaction of the one or more end effectors with the target tissue as the procedure is performed. In the case of a minimally invasive surgical procedure, the imaging device may include an endoscope or stereoscopic endoscope that is inserted into the patient through a corresponding port. In some examples, the location of the imaging device may be set to a default location determined based on the procedure to be performed (e.g., using a port located at the umbilicus for an upper abdominal procedure), operator preference, operator direction, and/or the like. In some examples, in addition to identification of the placement of the imaging device, additional information associated with the imaging device may be obtained including one or more of a model of the imaging device, a direction of view of the imaging device, a field of view of the imaging device (e.g., a range of angles relative to a direction of view access that may be captured using the imaging device, an aspect ratio of images captured by the imaging device, an actual or perceived working distance between the imaging device and the target anatomy and/or target workspace, and/or the like).

At a process 350, each of the possible port locations identified during process 320 is iterated through to evaluate its suitability as a port location. As each of the possible port locations is considered, the analyses of processes 352-356 are repeated to determine metrics usable to characterize corresponding aspects of each of the port locations as to level of suitability for use with the contemplated procedure.

At a process 352, a reachability metric is determined for a port location. The reachability metric is a kinematic measure of how well the target tissue and/or the target workspace identified during process 330 may be reached using an instrument inserted into the workspace via the port location. In some embodiments, the reachability metric may address the ability of the instrument to reach the target tissue from the port location. In some examples, the reachability metric may be determined by determining an articulation volume (also called a reachable swept volume) within the patient anatomy that is reachable by an end effector (e.g., end effector 274) by articulating an elongate shaft (e.g., elongate shaft 272) of an instrument (e.g., instrument 270) through a roughly conical space with an apex at the port location (e.g., remote center 280) as the pitch, yaw, and level of insertion are varied. In some examples, when the instrument includes an articulated wrist (e.g., articulated wrist 276), the reachable swept volume may additionally include points reachable by articulating the articulated wrist as the pitch, yaw, and level of insertion of the instrument are also adjusted. In some examples, the pitch and/or yaw may be limited by range of motion limits of the instrument or the manipulator to which the instrument is mounted and/or the insertion depth may be limited by a length of the elongate shaft and/or the relative location of the remote center relative to the manipulator. In some examples, additional factors that may further limit the reachable swept volume include the capabilities of the computer-assisted device, a current position and/or orientation of one or more joints of the computer-assisted device, a model of the computer-assisted device, an orientation of the patient, an orientation of an operating table on which the patient is placed, a location of the computer-assisted device relative to the patient, and/or the like. In some examples, one or more kinematic models of the instrument and/or the manipulator to which the instrument is mounted may be used to determine the reachable swept volume.

In some embodiments, the reachability metric may address the ability of the instrument to reach and maneuver around the target tissue from the port location and may be characterized as an ability to reach a dexterous workspace related to the target workspace identified during process 320. In some examples, a dexterous swept volume similar to the reachable swept volume described above may be determined with points in the dexterous swept volume being additionally limited to those points in the workspace that may be reached subject to the ability of the points to be reached over a range of articulations in the articulated wrist. In some examples, one or more kinematic models of the instrument and/or the manipulator to which the instrument is mounted may be used to determine the dexterously reachable swept volume.

In some examples, the reachability metric may be a binary pass-fail metric indicating whether the target tissue is reachable and/or dexterously reachable using the instrument from the port location. In some examples, the reachability metric may an analog value, such as in the range between 0 and 1 inclusive, indicating a relative quality of the reachability and/or the dexterous reachability. In some examples, the analog value may be assigned based on how much of the target tissue is reachable by the instrument from the port location (e.g., how much of the target tissue is within the reachable swept volume). In some examples, the analog value may be assigned based on how much of the insertion range of the instrument is used to reach the target tissue with 0 representing not reachable and 1 representing that the instrument may reach the target tissue from the port location using a predetermined percentage of the full insertion. In some examples, the analog value may be determined based on how far the target tissue is from half the full insertion of the instrument according to Equation 1, where the full insertion is length L and the distance between the port location and the target tissue is d. In some examples, other equations may be used.

$$\text{Length Analog Reachability Metric} = 1 - |d - 0.5L|/0.5L \quad \text{Equation 1}$$

In some examples, the analog value may be determined based on how far the target tissue is from the center line of the swept volume so that when the target tissue is closer to the center line of the swept volume, the higher the corresponding reachability metric. In some examples, the analog value may be determined according to Equation 2, where a is the angle between the center line of the swept volume and the line between the port location and the target tissue and A is the largest pitch and/or yaw angle of the instrument. In some examples, other equations may be used that favor target tissue locations closer to the center line.

$$\text{Angle Analog Reachability Metric} = a/A \quad \text{Equation 2}$$

In some examples, the length and angle analog reachability metrics may both be used with their values being combined using any triangular norm function, such as minimum, multiplication, and/or the like.

At a process 354, a collision volume is determined. In order to manipulate the instrument within the workspace, one or more portions of the instrument and/or the manipulator to which the instrument is mounted that are proximal to the port location are also subject to motion that results in the one or more portions of the instrument and/or the manipulator to which the instrument is mounted moving through a swept volume (also referred to as a collision volume or region of activity) external to the patient and/or the workspace. When more than one instrument and corresponding manipulator and/or repositionable arm are used, overlaps between their respective collision volumes indicate a potential for collisions during a procedure. In some examples, the collision volume for the port location may be determined by using one or more kinematic models of the instrument, the manipulator to which the instrument is mounted, and/or the repositionable arm to which the manipulator is mounted and noting that collision volume as the instrument is manipulated through its complete range of motion through the port location. In some examples, the portions of the instrument, manipulator, and/or repositionable arm used to generate the collision volume may be a subset of the joints and linkages of instrument, manipulator, and/or repositionable arm, such as only spar 278 in the examples of FIG. 2.

Figure 4A:
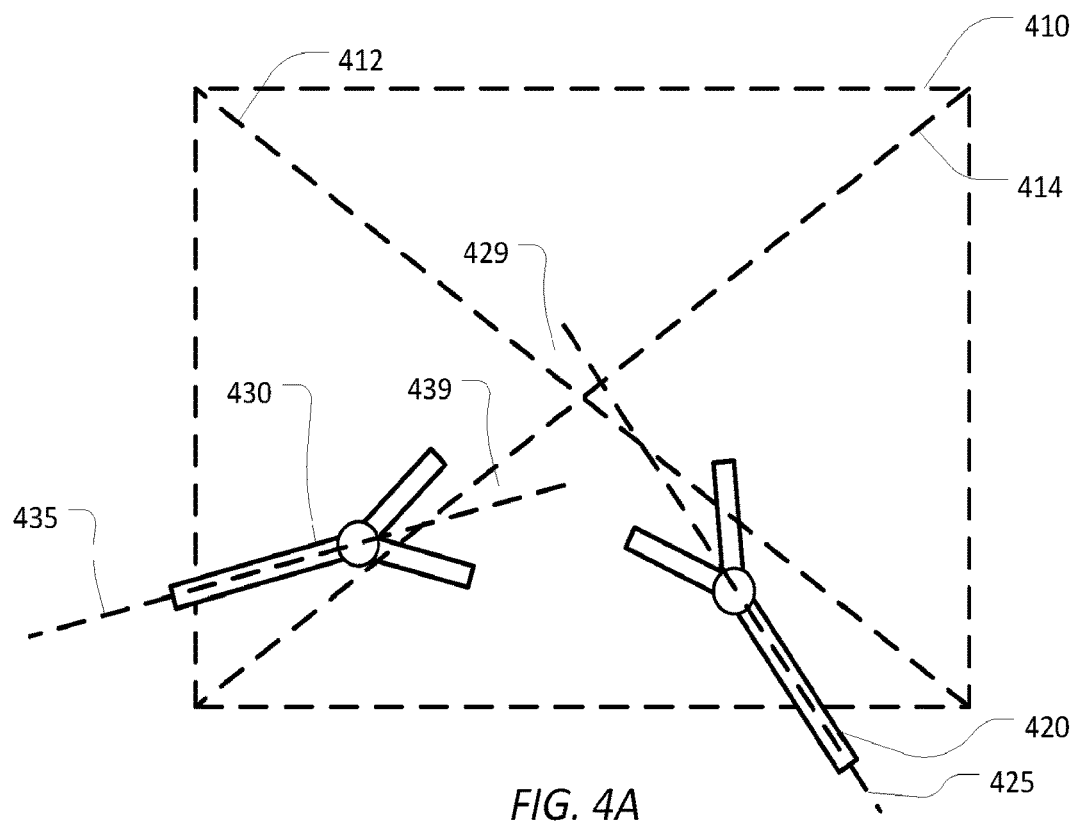
FIGS. 4A and 4B are simplified diagrams of different end effector positions and orientations within a workspace according to some embodiments.
Figure 4B:
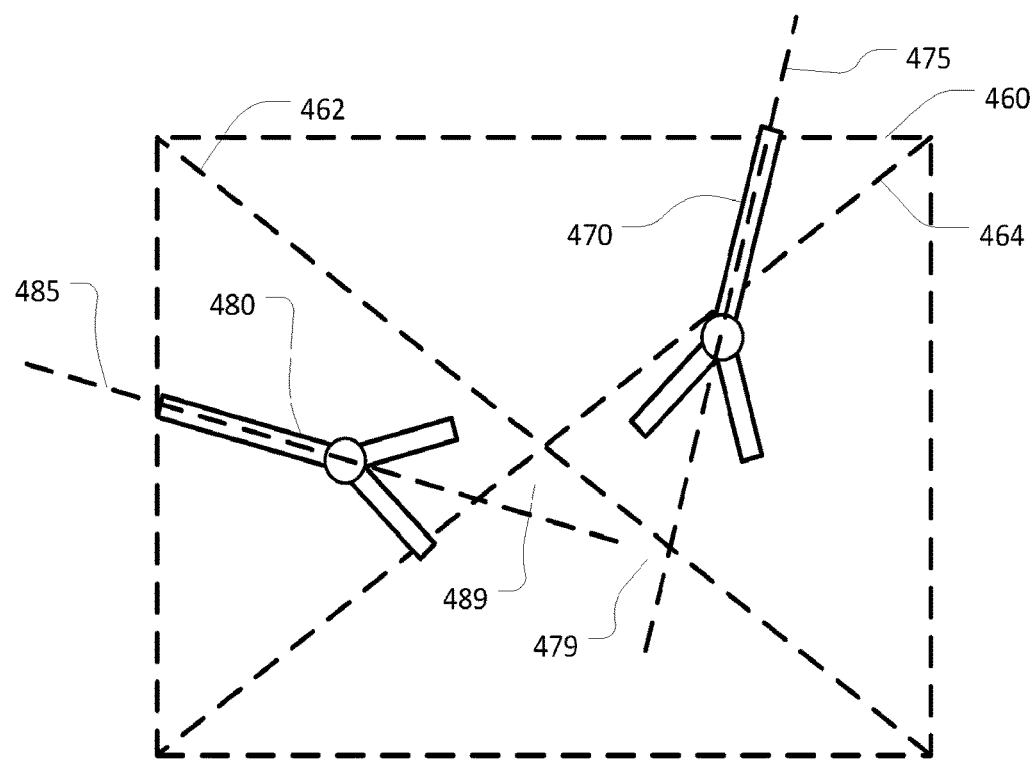

At a process 356, an anthropomorphic metric for the port location is determined. The anthropomorphic metric captures the ease with which the operator may manipulate the end effector to the target tissue and manipulate the end effector around the target tissue using the port location. In some examples, when the instrument and the end effector are to be operated so that motion of an input control device relative to a display device (e.g., input control device 195 and display system 180 in the examples of FIG. 1) results in corresponding motion of the instrument and end effector (e.g., the instrument and end effector move as if they are an instrument held in the operator's hand), the most natural approach toward the workspace may be to bring the end effector toward the target tissue from the lower left (as if held in the left hand) or from the lower right (as if held in the right hand). These concepts are shown in FIGS. 4A and 4B, which are simplified diagrams of different end effector positions and orientations within a workspace according to some embodiments. FIG. 4A shows a view 410 of a workspace that may be captured by the imaging device whose placement was determined during process 340 and whose end effectors are introduced into the workspace using a first set of port locations. In some examples, view 410 may be obtained by placing the imaging device at a known imaging distance from the target tissue, which is placed at the center of view 410. Two planes (shown as projected lines in FIG. 4A) indicate the main diagonals 412 and 414 of view 410 and may roughly correspond to the ideal approach directions for instruments and/or end effectors. Also shown in FIG. 4A is a first end effector 420 that approaches a center point of the workspace along an insertion axis 425. A difference between insertion axis 425 and main diagonal 412 of view 410 is shown as angle 429. FIG. 4A also shows a second end effector 430 that approaches a center point of the workspace along an insertion axis 435. A difference between insertion axis 435 and main diagonal 414 of view 410 is shown as angle 439.

As another example, FIG. 4B shows another view 460 of a workspace that may be captured by the imaging device whose placement was determined during process 340 and whose end effectors are introduced into the workspace using a second set of port locations. In some examples, view 460 may be obtained by placing the imaging device at a known imaging distance from the target tissue, which is placed at the center of view 460. Two planes (shown as projected lines in FIG. 4B) indicate the main diagonals 462 and 464 of view 460 and may roughly correspond to the ideal approach directions for instruments and/or end effectors. Also shown in FIG. 4B is a first end effector 470 that approaches a center point of the workspace along an insertion axis 475. A difference between insertion axis 475 and main diagonal 462 of view 460 is shown as angle 479. FIG. 4B also shows a second end effector 480 that approaches a center point of the workspace along an insertion axis 485. A difference between insertion axis 485 and main diagonal 464 of view 460 is shown as angle 489.

Because angles 429 and 439 are smaller than angles 479 and 489, they indicate that end effectors 420 and 430 are approaching the center point of the workspace more naturally than end effectors 470 and 480. Thus, the first set of port locations, which are associated with end effectors 420 and 430 are considered more anthropomorphic and are assigned a higher anthropomorphic metric than the second set of port locations. In some examples, the anthropomorphic metric for a port location may be determined using either Equation 3 or Equation 4, where b corresponds to the angle between the insertion axis of the end effector from the port location and the main diagonal.

$$\text{Anthropomorphic Metric} = (90 - b)/90 \qquad \text{Equation 3}$$

$$\text{Anthropomorphic Metric} = (180 - b)/180 \qquad \text{Equation 4}$$

In some examples, the additional information obtained regarding the imaging device during process 340 (e.g., the imaging device type, the aspect ratio, the field of view, the working distance, and/or the like) may be used to help position views 410 and/or 460 as well as to determine the orientations of the main diagonals 412, 414, 462, and/or 464.

In some embodiments, the anthropomorphic metric may also account for a human factors constraint, such as a handedness preference of the operator. In some examples, when the operator indicates a preference for a particular instrument to be used in a specific hand then the angle used for the anthropomorphic metric should be determined using the main diagonal for that hand (e.g., main diagonal 412 and/or 462 for a right-handed instrument and main diagonal 414 and/or 464 for a left handed instrument) even though the other main diagonal may have a smaller angle relative to the insertion axis of the instrument. In some examples, both right- and left-handed anthropomorphic metrics may be determined for the port location so that both right- and left-handed evaluations may be considered during the remainder of method 300.

Referring back to FIG. 3, at a process 360, each of the possible combinations of port locations identified during process 320 is iterated through to evaluate the suitability of the combination of port locations for a procedure. When the procedure is to be performed using two instruments then each combination of port locations includes two port locations. And more generally, when the procedure is to be performed using n instruments (n being equal to 3, 4, or more) then each combination of port locations includes n port locations. As each of the possible combinations of port locations is considered, the analyses of processes 362 and 364 are repeated to determine aggregate scoring metrics usable to characterize the suitability of the combination of port locations for use with the contemplated procedure.

At a process 362, a collision metric is determined for the combination of port locations. The collision metric is a kinematic measure providing an indication of how likely or unlikely collisions are to occur in the portions of the instruments, manipulators, and/or repositionable arms located proximal to the port locations in the combination. In some examples, the collision metric may be determined based on an amount of overlap between the collision volumes determined during process 354 for each of the port locations in the combination. Where more overlap in the collision volumes occurs, the likelihood of a collision increases and the collision metric decreases. In some examples, the collision metric may be determined based on a percentage of overlap of each of the collision volumes by other collision volumes. In some examples, the percentage of overlap of a collision volume by other collision volumes is determined based on the ratio of the total collision volume that is overlapped by other collision volumes and the total collision volume. In some examples, this may be converted to an overlap metric as shown in Equation 5.

$$\text{Overlap Metric} = 1 - (\text{overlapped } CV)/(\text{total } CV) \qquad \text{Equation 5}$$

When the combination of port locations includes two port locations, the overlap metric may be used as the collision metric. When the combination of port locations includes three or more port locations, the collision metric may be determined by using an aggregation of the overlap metrics for each of the corresponding collision volumes. In some examples, the overlap metrics for each of the corresponding collision volumes may be aggregated using any triangular norm function, such as minimum, multiplication, and/or the like.

At a process 364, an aggregate scoring metric is determined for the combination of port locations. In some examples, the aggregate scoring metric may be determined by aggregating together the reachability metric for each of the port locations in the combination, the anthropomorphic metric for each of the port locations in the combination, and the collision metric for the combination. In some examples, the aggregation may be performed using a weighted sum with the weights being pre-assigned and/or adjustable by an operator. In some examples, a weight of zero may be used to omit a corresponding metric from the aggregation. In some examples, the aggregation may be determined by combining the metrics using any triangular norm function, such as minimum, multiplication, and/or the like. In some examples, the aggregate scoring metric may be used to indicate the suitability of the combination of port locations relative to other combinations of port locations.

At a process 370, one or more of the combinations of port locations are displayed to an operator. In some examples, a combination of port locations and a corresponding evaluation may be displayed to the operator using any suitable display device include a tablet, a computer screen, a simulator, and/or the like. In some examples, the combination of port locations and the corresponding evaluation may be displayed as a two-dimensional projection, a three-dimensional image on a stereoscopic display and/or the like. In some examples, the order in which the combinations of port locations may be displayed may be based on their relative aggregate scoring metrics, with the highest scoring combination being displayed first. In some examples, one or more lists, menus, and/or the like may be used to allow the operator to select from among the evaluated combinations. In some examples, the corresponding evaluation may be displayed as one or more text lines indicating the values determined for each of the reachability, anthropomorphic, and/or collision metrics along with the aggregate scoring metric. In some examples, the one or more text lines may indicate the relative weighting of each metric and optionally provide mechanisms for the operator to adjust the weights. In some examples, one or more mechanisms for adding additional constraints (e.g., human factors constraints such as handedness of one of the instruments) may also be provided.

Figure 5:
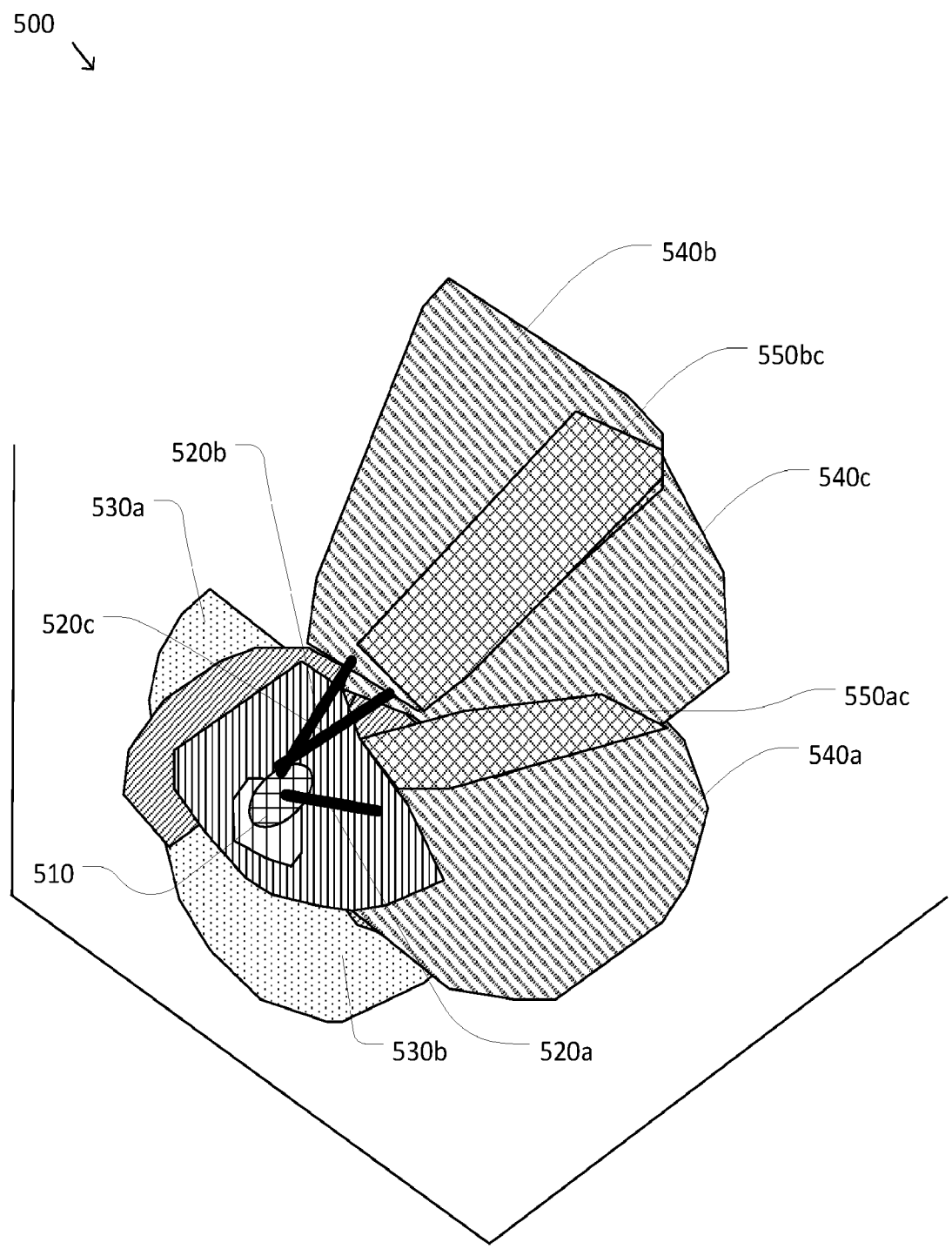
FIG. 5 is a simplified diagram of a combination of port locations according to some embodiments.

FIG. 5 is a simplified diagram 500 of a combination of port locations according to some embodiments. As shown in FIG. 5, diagram 500 includes information on a three-port combination about target tissue 510. The elongated shaft of each of the instruments is depicted using simplified representations 520a-520c. Also shown are the reachable swept volumes 530a and 530b for instruments a and b, respectively. The reachable swept volume for instrument c is omitted from FIG. 5 for the purposes of readability, but may also be included in FIG. 5. The collision volumes 540a-540c for each of the instruments are also shown. Further, the overlaps in collision volumes 540a-540c are also depicted as overlap volumes 550ac (for the overlap between collision volumes 540a and 540c) and 550bc (for the overlap between collision volumes 540b and 540c). As can be observed, FIG. 5 provides a helpful visualization tool for understanding aspects of the aggregate scoring metric determination and helps provide feedback to the operator regarding both reachability and/or the likelihood of collisions. In some examples, the orientation of diagram 500 may be changed so that the operator may view the evaluation of the combination of port locations from multiple perspectives. In some examples, the interface for diagram 500 may also provide mechanisms for suppressing one or more of the elements, such as any of the swept volumes, and/or the like. In some examples, diagram 500 may represent one of multiple panes, with each of the panes being usable to display a different combination of port locations to provide support for side-by-side comparisons.

Referring back to FIG. 3, at a process 380, port location selections are received from the operator. In some examples, the port location selections may be selected by indicating that a current combination of port locations being displayed (e.g., using process 370) is the selected combination. In some examples, other selection mechanisms may be used, such as selecting from a list, and/or the like.

At a process 390, guidance is provided to the operator for the placing of ports at the port locations selected during process 380. In some examples, the guidance for the placing of a port at one of the selected port locations may include one or more of laser targets projected on the port locations, pointing to the port location using the manipulator, projections onto the patient, haptic guidance for manual positioning of the manipulator, augmented reality overlays on a stereoscopic image of the patient, and/or the like.

According to some embodiments, factors and/or options other than the port locations may also have a significant impact on the various metrics considered during method 300. In some examples, the location and/or positioning of the computer-assisted device relative to the patient may significantly impact the various reachability, collision, and/or other metrics. In some examples, a computer-assisted device mounted on a mobile cart may be placed on different sides of a patient and/or workspace, placed at different positions along an operating table and/or the workspace, placed at different orientations relative to the operating table and/or the workspace, and/or the like. In some examples, a computer-assisted device that is mounted to the workspace (e.g., onto the operating table) may be mounted at different locations and/or orientations. In some examples, different computer-assisted devices and/or instruments may be available for a procedure with the kinematic structure of each also impacting the various reachability, collision, and/or other metrics. Accordingly, systems and methods for considering device placement, device type, and/or the like would be advantageous.

Figure 6:
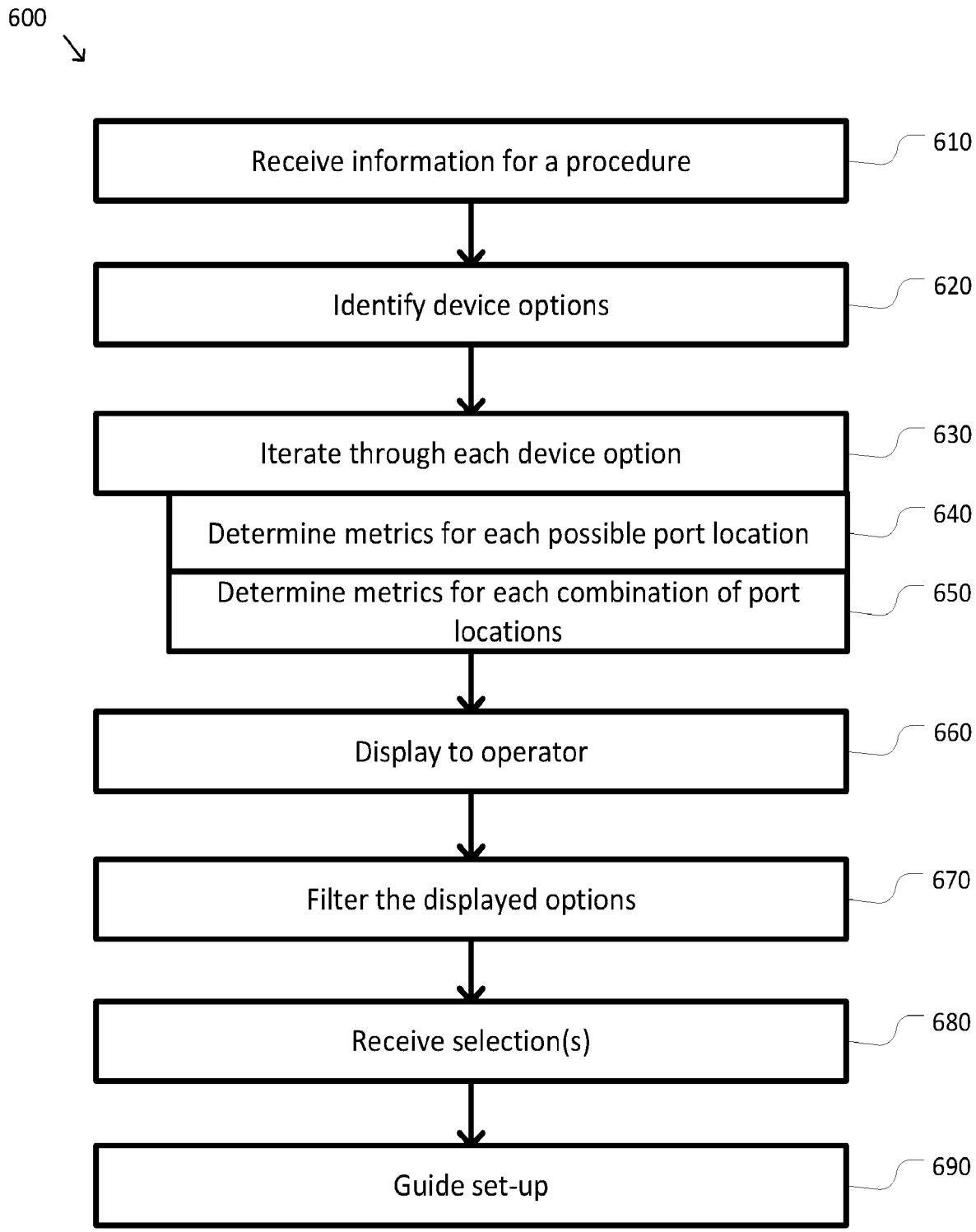
FIG. 6 is a simplified diagram of a method of selecting device and port locations according to some embodiments.

FIG. 6 is a simplified diagram of a method of selecting device and port locations according to some embodiments. One or more of the processes 610-690 of method 600 may be implemented, at least in part, in the form of executable code stored on non-transitory, tangible, machine-readable media that when run by one or more processors (e.g., the processor 140 in control unit 130) may cause the one or more processors to perform one or more of the processes 610-690. In some embodiments, method 600 may be performed by a module, such as port placement module 160. In some embodiments, method 600 may be used to consider various device options, identify port locations, evaluate each of the port locations in view of the device options, evaluate combinations of port locations, aid an operator in selecting and utilizing suitable device options and port locations, and/or the like. In some examples, method 600 may be used to evaluate combinations of device options and port locations for one or more instruments, such as instrument 270, being teleoperated using a computer-assisted device, such as computer-assisted device 200. In some embodiments, process 670 is optional and may be omitted.

At a process 610, information for a procedure is received. In some examples, process 610 may include one or more of receiving a patient model, identifying possible port locations, identifying a target workspace, identifying an imaging device placement, and/or the like. In some examples, process 610 may include performing one or more of processes 310-340.

At a process 620, device options are identified. In some examples, the device options may include one or more of possible locations for a base for the computer-assisted device to be used to perform the procedure, one or more possible choices in computer-assisted devices, one or more possible choices in repositionable arms, one or more possible choices in manipulators that may be mounted to the repositionable arms, one or more possible options for instruments that may be mounted to the manipulators and used to perform portions of the procedure. In some examples, the possible locations for the base of the computer-assisted device may include possible locations and/or orientations of a rolling cart relative to a workspace (e.g., a surgical table), possible locations for the mounting of the computer-assisted device relative to the workspace. In some examples, the possible locations for the mounting of the computer-assisted device may include one or more of possible mounting locations on a floor, on a ceiling, on a rack, on the workspace (e.g., on the surgical table), and/or the like. In some examples, the possible locations for the base of the computer-assisted device may include selecting from different possible locations for respective bases of each of the repositionable arms. In some examples, the possible choices in the repositionable arms may include options from among repositionable arms of different models, types, configurations, and/or the like that may be selectively mounted to the computer-assisted device. In some examples, the possible choices in the manipulators may include options from among manipulators of different models, types, configurations, and/or the like that may be selectively mounted to the repositionable arms. In some examples, the possible choices in the instruments may include options from among instruments of different models, types, configurations, and/or the like that may be selectively mounted to the manipulators. In some examples, the instruments may include one or more medical instruments, imaging devices, tools, and/or the like.

In some examples, the medical instruments may include clamps, grippers, retractors, cautery tools, suction tools, suturing devices, and/or the like. In some medical examples, the imaging devices may include endoscopes, cameras, ultrasonic devices, fluoroscopic devices, and/or the like.

At a process 630, each of the possible device options identified during process 620 is iterated through to evaluate its suitability for the proposed procedure. In some examples, each of the possible options may include combinations of one or more of the possible locations for the base for the computer-assisted device, one or more of the possible computer-assisted devices, one or more of the possible choices in repositionable arms, one or more of the possible choices in manipulators, and/or one or more of the possible choices in instruments. As an example, one of the possible device options may include selecting from a mounting location for each of four repositionable arms on the workspace, a type of each of the repositionable arms, a type of each of the manipulators, and a type of each of the instruments. As another example, one of possible device options may include selecting a position and orientation for the rolling cart, a type of each of the manipulators, and a type of each of the instruments. As another example, one of the possible device options may include selecting a position and orientation for the rolling cart of a first type of computer-assisted device, a type of each of the manipulators on the first type of computer-assisted device, a mounting location for a second type of computer-assisted device, a type of repositionable arm for the second type of computer-assisted device, a type of each instrument used with the first and second types of computer-assisted device, etc. Other examples are possible as would be apparent to one of skill of the art and/or an operator from among the available device options. As each of the possible device options is considered, the analyses of processes 640 and 650 are repeated to determine metrics usable to characterize corresponding aspects of each of the device options, port locations, and combinations of port locations as to their level of suitability for use with the contemplated procedure.

At a process 640, metrics for each of the possible port locations are determined. Metrics for each of the possible port locations are considered by iterating through each possible port location to determine various metrics, such as a reachability metric, a collision volume, an anthropomorphic metric, and/or the like. In some examples, one or more of the various metrics may be affected by the combination of the locations for the base of the computer-assisted device, a choice of the computer-assisted device, a choice of the repositionable arms, a choice of the manipulators, and/or a choice of the instruments. In some examples, process 640 may include performing processes 350-356.

At a process 650, metrics for each of the possible combinations of port locations are determined. Metrics for each of the possible combinations of port locations are considered by iterating through each possible combination of port locations to determine various metrics, such as a collision metric, an aggregate scoring metric, and/or the like. In some examples, one or more of the various metrics may be affected by the combination of the locations for the base of the computer-assisted device, a choice of the computer-assisted device, a choice of the repositionable arms, a choice of the manipulators, and/or a choice of the instruments. In some examples, process 650 may include performing processes 360-364.

At a process 660, one or more of the combinations of device options and combinations of port locations are displayed to an operator. In some examples, a combination of device options and combination of port locations along with a corresponding evaluation may be displayed to the operator using any suitable display device include a tablet, a computer screen, a simulator, and/or the like. In some examples, the combination of device options and port locations and the corresponding evaluation may be displayed as a two-dimensional projection, a three-dimensional image on a stereoscopic display and/or the like. In some examples, the order in which the combinations of device options and combinations of port locations may be displayed may be based on their relative aggregate scoring metrics, with the highest scoring combination being displayed first. In some examples, one or more lists, menus, and/or the like may be used to allow the operator to select from among the evaluated combinations. In some examples, the corresponding evaluation may be displayed as one or more text lines indicating the options included in the corresponding combination along with values determined for each of the reachability, anthropomorphic, and/or collision metrics along with the aggregate scoring metric. In some examples, the one or more text lines may indicate the relative weighting of each metric and optionally provide mechanisms for the operator to adjust the weights. In some examples, one or more mechanisms for adding additional constraints (e.g., human factors constraints such as handedness of one of the instruments) may also be provided. In some examples, each of the combinations may be displayed with a diagram similar to diagram 500 to give a visual indication of the how the combination affects each of the various metrics.

At an optional process 670, the displayed options may be filtered. As a large number of evaluated combinations are possible, various filtering tools and/or options may be provided to reduce the number of options displayed by process 660. In some examples, the filtering may include choices for eliminating options (e.g., any of the device options, port locations, and/or combinations of port locations), selecting one or more options to evaluate the variations from the other options (e.g., selecting a type of computer-assisted device to evaluate the options available using just that computer-assisted device), and/or the like. In some examples, the filtering may include sorting options so that the operator may categorize, organize, and/or consider the various options using a suitable grouping and/or ordering preferred by the operator.

At a process 680, one or more selections are received from the operator. In some examples, the one or more selections may include a selection of one of the device options and one of the combinations of port locations. In some examples, the operator may indicate the one or more selections by indicating that a current combination of device options and port locations being displayed (e.g., using process 660) is the selected combination. In some examples, other selection mechanisms may be used, such as selecting from a list, and/or the like.

At a process 890, guidance is provided to the operator for setting up the computer-assisted device and the combination of port locations selected during process 680. In some examples, the guidance may include guidance and/or other feedback to aid the operator in selecting the computer-assisted device, placing the computer-assisted device in or near the workspace, mounting one or more repositionable arms, mounting one or more manipulators, and/or mounting one or more instruments. In some examples, the guidance may include providing feedback as to whether a detected computer-assisted device, repositionable arm, manipulator, and/or instrument matches or does not match the selections from process 680. In some examples, the guidance may include guidance regarding the configurations and/or placements of the repositionable arms, manipulators, and/or instruments after mounting, such as by providing written instructions, verbal instructions, haptic feedback, activation of indicators on the correct elements, pointers, spot lights, and/or the like. In some examples, the guidance for the placing of a port at one of the selected port locations may include one or more of laser targets projected on the port locations, pointing to the port location using the manipulator, projections onto the patient, haptic guidance for manual positioning of the manipulator, augmented reality overlays on a stereoscopic image of the patient, and/or the like.

As discussed above and further emphasized here, FIGS. 3 and 6 are merely examples which should not unduly limit the scope of the claims. One of ordinary skill in the art would recognize many variations, alternatives, and modifications. In some embodiments, one or more of the processes of method 300 may be performed in a different order than the order implied by the flow chart in FIG. 3. In some examples, processes 320-340 may be performed in any order. In some examples, processes 352-356 may be performed in different orders and/or concurrently. In some examples, processes 350-364 may be performed concurrently with processes 352-356 being performed for each port location being considered for a first time within one of the combinations of process 360. In some examples, process 370 and 380 may be performed iteratively to assist an operator in evaluating and selecting different port location combinations. In some examples, processes 360 and/or 364 may be re-performed during process 370 when the operator adjusts the aggregate scoring metric.

In some embodiments, the filtering of process 670 may be adaptively applied at other stages of methods 300 and/or 600. In some examples, process 670 may be performed concurrently and/or iteratively with processes 370 and/or 660 so that the operator may organize, sort, and/or filter the displayed combinations as different filtering options are selected and/or activated. In some examples, filtering may be used during any of processes 320-364 and/or 620-650 to limit the number of combinations that may be considered and/or evaluated. In some examples, the operator may limit the evaluation to one or more of certain types of computer-assisted device, certain locations for the base of the computer-assisted device, certain types and/or configurations of repositionable arms, certain types and/or configurations of manipulators, certain types and/or configurations of instruments, certain ports locations and/or ranges for port locations, and/or the like.

In some embodiments, other factors may also be considered in the aggregate scoring metric for a combination of port locations. In some examples, the ability of a manipulator to deliver an instrument to a port location may also be considered. In some examples, the ability of the manipulator to deliver an instrument to the port location may depend on reach, range of motion in the manipulator and/or repositionable arm remaining after the port location is reached, and/or the like.

In some embodiments, methods 300 and/or 600 may be adapted for other uses than the selection and guidance of port and/or device options. In some examples, methods 300 and/or 600 may be usable for pre-operative planning for a simulated patient where port locations may be moved around in a synthetic environment to see the effects of device choice, instrument choice, handedness, and/or other constraints. In some examples, methods 300 and/or 600 may be adapted to provide guidance to an operator regarding the impact of deviation in port locations from the selected port locations. In some examples, methods 300 and/or 600 may be adapted to allow the operator to constrain one or more of the port locations and/or device options and then to explore possibilities for the remaining port locations. In some examples, methods 300 and/or 600 may be adapted for intraoperative use to evaluate port locations after partial set-up of a computer-assisted device (e.g., after the location and orientation of orientation platform 227) to help optimize range of motion, to recommend alternate port locations for another segment of a procedure, to adapt to detection of additional target tissue locations, and/or the like.

In some embodiments, methods 300 and/or 600 may also be adapted to take advantage of information gathered intraoperatively and/or post operatively. In some examples, the reachability, dexterous reachability, anthropomorphicness, and/or collision likelihood could be evaluated by the operator with the evaluation being usable to adjust the parameters, weights, and/or the like for the various metrics. In some examples, tracking of procedures for various combinations of operators, procedures, and/or instruments may be used to determine more likely swept volumes for reachability, collision volumes, and/or the like based on actual volumes swept during the procedures. In some examples, the likelihood of volumes being swept may also be useable to provide a weighting field on the corresponding volumes to provide a more robust indicator of reachability, dexterous reachability, collision likelihood, and/or the like. In some examples, the insertion axis orientation for various operators, procedures, and/or instruments may also be tracked to determine a preferred orientation that may be different from the main diagonals of the imaging device view.

Some examples of control units, such as control unit 130 may include non-transitory, tangible, machine readable media that include executable code that when run by one or more processors (e.g., processor 140) may cause the one or more processors to perform the processes of methods 300 and/or 600. Some common forms of machine readable media that may include the processes of methods 300 and/or 600 are, for example, floppy disk, flexible disk, hard disk, magnetic tape, any other magnetic medium, CD-ROM, any other optical medium, punch cards, paper tape, any other physical medium with patterns of holes. RAM, PROM, EPROM. FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computing device comprising:
   a memory; and
   a control unit coupled to the memory and being configured to:
   receive a patient model;
   identify a plurality of port locations on the patient model for accessing a workspace using a plurality of instruments controlled by a computer-assisted device;

for each of the port locations, determine a collision volume for portions of the computer-assisted device proximal to the port location, a reachability metric, and an anthropomorphic metric;

for each combination of the plurality of port locations, determine a collision metric based on overlaps of the collision volumes for the port locations in the combination, and an aggregate metric for the combination; and display one or more of the combinations of the plurality of port locations to a user along with a corresponding aggregate metric.

2. The computing device of claim 1, wherein the reachability metric indicates an ability of an instrument to reach a target tissue using a corresponding port location.

3. The computing device of claim 1, wherein the reachability metric indicates an ability of an instrument to dexterously reach a target tissue using a corresponding port location.

4. The computing device of claim 1, wherein to determine the reachability metric the control unit is configured to determine a swept volume that corresponds to areas of the workspace that would be encountered as a corresponding instrument is manipulated through its degrees of freedom, the corresponding instrument being introduced into the workspace through the port location.

5. The computing device of claim 4, wherein the degrees of freedom include one or more of a pitch, a yaw, and an insertion distance.

6. The computing device of claim 5, wherein the degrees of freedom further include articulation degrees of freedom for an articulated wrist of the corresponding instrument.

7. The computing device of claim 4, wherein the reachability metric indicates how much of the swept volume is used to reach a target tissue or how much of a target tissue is within the swept volume.

8. The computing device of claim 4, wherein the collision volume corresponds to a volume swept by the portions of the computer-assisted device proximal to the port location.

9. The computing device of claim 8, wherein the portions of the computer-assisted device include a spar used as an insertion stage for a corresponding instrument introduced into the workspace through the port location.

10. The computing device of claim 1, wherein the anthropomorphic metric indicates an ease with which an operator may manipulate a corresponding instrument introduced into the workspace through the port location.

11. The computing device of claim 1, wherein the anthropomorphic metric is based on how close an insertion axis of a corresponding instrument introduced into the workspace through the port location is to a main diagonal of a view captured by an imaging device or is based on a hand by which a corresponding instrument introduced into the workspace through the port location is to be manipulated.

12. The computing device of claim 1, wherein the collision metric indicates a likelihood of collision between the portions of the computer-assisted device proximal to each of the port locations in the combination.

13. The computing device of claim 1, wherein to determine the collision metric the control unit is configured to determine overlaps between the collision volumes of each of the port locations in the combination.

14. The computing device of claim 1, wherein the aggregate metric is an aggregation of the reachability metrics of each of the port locations in the combination, the anthropomorphic metrics of each of the port locations in the combination, and the collision metric for the combination of port locations.

15. The computing device of claim 14, wherein the aggregation is a weighted sum or a triangular norm.

16. The computing device of claim 1, wherein to display a combination of the plurality of port locations the control unit is configured to display one or more of target tissue, reachability volumes for each of the port locations in the combination, collision volumes for each of the port locations in the combination, the reachability metrics of each of the port locations in the combination, the anthropomorphic metrics of each of the port locations in the combination, and the collision metric for the combination of port locations.

17. The computing device of claim 1, wherein the control unit is further configured to identify a placement of an imaging device within the workspace.

18. The computing device of claim 17, wherein to identify the imaging device placement the control unit is configured to identify one or more of a type of the imaging device, an aspect ratio of the imaging device, a field of view of the imaging device, and a working distance of the imaging device.

19. The computing device of claim 17, wherein the control unit is further configured to:
receive a selection of a first combination of port locations from the one or more combinations of the plurality of port locations; and
provide guidance to the user for placing ports at each of the port locations in the first combination.

20. The computing device of claim 1, wherein each port location corresponds to a remote center of a corresponding instrument introduced into the workspace through the port location.

* * * * *